US00PP11981P2

(12) United States Plant Patent
Fruehwirth

(10) Patent No.: US PP11,981 P2
(45) Date of Patent: Jul. 10, 2001

(54) POINSETTIA PLANT NAMED 'ECKADOLFO'

(75) Inventor: Franz Fruehwirth, Encinitas, CA (US)

(73) Assignee: Paul Ecke Ranch, Encinitas, CA (US)

( * ) Notice: Subject to any disclaimer, the term of this patent is extended or adjusted under 35 U.S.C. 154(b) by 0 days.

(21) Appl. No.: 09/345,563

(22) Filed: Jun. 30, 1999

(51) Int. Cl.[7] ..... A01H 5/00

(52) U.S. Cl. ..... Plt./306

(58) Field of Search ..... Plt./306, 307, 303

(56) References Cited

PUBLICATIONS

UPOV–ROM GTIM Computer Database 2000/02, GTI Jouve Retrieval Software, citation for 'Eckadia', Mar. 1998.*

* cited by examiner

*Primary Examiner*—Bruce R. Campell
*Assistant Examiner*—Anne Marie Grün berg
(74) *Attorney, Agent, or Firm*—C. A. Whealy

(57) ABSTRACT

A new and distinct cultivar of Poinsettia plant named 'Eckadolfo', characterized by its dark coral pink bracts; green. light green and light yellow variegated leaves; compact, upright and spreading plant habit; very freely branching habit; and excellent postproduction longevity.

2 Drawing Sheets

BACKGROUND OF THE INVENTION

The present invention relates to a new and distinct cultivar of Poinsettia plant, botanically known as *Euphorbia pulcherrima* Willd., and hereinafter referred to by the name 'Eckadolfo'.

The new Poinsettia is a naturally-occurring mutation of the commercial *Euphorbia pulcherrima* Willd. cultivar 'Beckmanns Altrosa', disclosed in U.S. Plant Pat. No. 9,336. The new Poinsettia was selected by the Inventor in a greenhouse in Encinitas, Calif., in 1997. The objective of the Inventor's Poinsettia development program is to create new Poinsettia cultivars having interesting bract and leaf display, desirable bract and foliage color and form, strong and freely branching stems and good post-production longevity.

Asexual reproduction of the new Poinsettia by terminal cuttings taken at Encinitas, Calif., has shown that the unique features of this new Poinsettia are stable and reproduced true to type in successive generations of asexual reproduction.

BRIEF SUMMARY OF THE INVENTION

The following traits have been repeatedly observed and are determined to be the unique characteristics of 'Eckadolfo'. These characteriestics in combination distinguish 'Eckadolfo' as a new and distinct cultivar:

1. Dark coral pink bracts.
2. Green, light green and light yellow variegated leaves.
3. Compact, upright and spreading plant habit.
4. Very freely branching habit.
5. Excellent postproduction longevity.

In side-by-side comparison conducted in Encinitas, Calif., plants of the new Poinsettia differed from plants of the parent cultivar, 'Beckmanns Altrosa', primarily in leaf coloration as leaves of plants of 'Beckmanns Altrosa' are not variegated.

The new Poinsettia can be compared to the nonvariegated commercial cultivar 'Peterstar Pink', disclosed in U.S. Plant Pat. No. 9,879. In side-by-side comparisons conducted in Encinitas, Calif., plants of the new Poinsettia differed from plants of 'Peterstar Pink' in the following characteristics:

1. Plants of the new Poinsettia are more compact, have shorter laterals and more rounded in plant shape than plants of 'Peterstar Pink'.

2. Plants of the new Poinsettia have slightly larger and flatter inflorescences than plants of 'Peterstar Pink'.

3. Flower bracts of plants of the new Poinsettia and 'Peterstar Pink' differ in color.

BRIEF DESCRIPTION OF THE PHOTOGRAPHS

The accompanying colored photographs illustrate the overall appearance of the new Poinsetttia, showing the colors as true as it is reasonably possible to obtain in colored reproductions of this type.

The photograph on the first sheet comprises a side perspective view of a typical plant of 'Eckadolfo'.

The photograph at the top of the second sheet comprises a top perspective view of a typical plant of 'Eckadolfo'.

The photograph at the bottom of the second sheet is a close-up view of typical bracts and leaves of 'Eckadolfo' (left) and 'Peterstar Pink' (right).

DETAILED BOTANICAL DESCRIPTION

The new Poinsettia has not been observed under all possible environmental conditions. The phenotype may vary somewhat with variations in environment such as temperature, daylength and light intensity, without, however, any variance in genotype. The following observations and measurements describe plants grown in Encinitas, Calif., under commercial practice in a polyethylene-covered greenhouse with day temperatures about 22 to 24° C., night temperatures about 16 to 18° C., and light levels about 4,000 foot-candles. Plants were grown in 16.5-cm pots, pinched one time, and flowered under naturally lengthening nights during the fall/early winter.

In the following description, color references are made to The Royal Horticultural Society Colour Chart except where general terms of ordinary dictionary significance are used.

Botanical classification: *Euphorbia pulcherrima* Willd. 'Eckadolfo'.

Parentage: Naturally-occurring mutation of *Euphorbia pulcherrima* Willd. cultivar 'Beckmanns Altrosa', disclosed in U.S. Plant Pat. No. 9,336.

Propagation:

*Type cutting.*—Terminal cuttings.

*Time to initiate roots.*—Summer: About 12 to 18 days at 26 to 28° C. Winter: About 15 to 18 days at 24° C.

*Time to develop roots.*—Summer: About 26 days at 26 to 28° C. Winter: About 26 days at 24° C.

*Rooting habit.*—Thick, freely branching, becoming fibrous with development.

Plant description:

*Plant form.*—Inverted triangle, top of plant rounded; mounding.

*Growth habit.*—Compact, upright and spreading. Very freely branching. Branching is enhanced by removing the shoot apex.

*Plant vigor.*—Moderate.

*Plant height.*—About 21 cm.

*Crop time.*—From unrooted cuttings to a flowering plant in a 16.5-cm container, about 17 weeks are required.

*Stem description.*—Number of lateral branches: About eight or nine lateral branches are formed after removal of the terminal apex. Lateral branch length: About 15 cm. Internode length: About 1.75 cm. Stem color: 146A.

*Foliage description.*—Quantity of leaves per lateral branch: About 7. Length: About 10.5 cm. Width: About 6.75 cm. Shape: Mostly ovate, very occasionally lobed. Apex: Acuminate. Base: Acute. Margin: Entire but some irregular indentations. Texture: Smooth, velvety, somewhat rugose. Mostly glabrous with very slight pubescence on lower surface. Color: Variegated; tri-colored with green, light green and light yellow coloration. Green colors towards center of leaf with light yellow coloration towards margins. Young foliage, upper surface: 138A, 138B and 4C. Young foliage, lower surface: 138B and 4C. Mature foliage, upper surface: 137A, 138B and 4C. Mature foliage, lower surface: 138A and 4C. Venation, upper surface: 145A. Venation, lower surface: 138D. Petiole: Length: About 6.25 cm. Diameter: About 2 mm. Color: Upper surface, 50C; lower surface, 138B.

Inflorescence description:

*Inflorescence type and habit.*—Inflorescences are compound corymbs of cyathia with colored flower bracts subtending the cyathia.

*Natural flowering season.*—Autumn/winter in Northern Hemisphere. Flower initiation and development can be induced under long night conditions. Response time is about 8.5 weeks.

*Quantity of inflorescences.*—One per lateral branch, usually about eight per plant.

*Inflorescence size.*—Diameter: About 30 cm. Height (depth): About 4.5 cm.

*Flower bracts.*—Quantity of flower bracts per inflorescence: Usually about 16 primary bracts and about 6 smaller secondary bracts per inflorescence. Length, largest bracts: About 15 cm. Width, largest bracts: About 10 cm. Shape: Ovate. Apex: Acuminate. Base: Acute. Margin: Entire. Texture: Somewhat rugose becoming smoother with development. Aspect: Mostly flat. Color: Developing, upper surface: 50A. Developing, lower surface: 50B. Mature, upper surface: 51A; fading to 51B with subsequent development. Mature, lower surface: 39C.

*Cyathia.*—Quantity: Usually about 15 per corymb. Diameter of cyathia cluster: About 2.5 by 3.5 cm. Length: About 1 cm. Width: About 5 mm. Color: Immature: 144A. Mature: 144B. Peduncle: Length: About 4 mm. Aspect: Strong, erect. Color: 144B. Stamens: Stamen number: Very numerous, typically more than 20 per cyathium. Anther size: Less than 1 mm. Anther shape: Oval. Anther color: 26C. Amount of pollen: Scarce. Pollen color: 10B. Pistils: Pistil number: 1. Pistil length: About 8 mm. Style length: About 4 mm. Style color: 144B to 144C. Stigma color: 45B. Nectary color: 23A. Seed set: Not observed.

Disease resistance: No fungal, bacterial nor viral problems observed on plants grown under commercial conditions.

Postproduction longevity: Generally plants maintain good substance and bract color for about six weeks under interior conditions.

It is claimed:

1. A new and distinct cultivar Poinsettia plant named 'Eckadolfo', as illustrated and described.

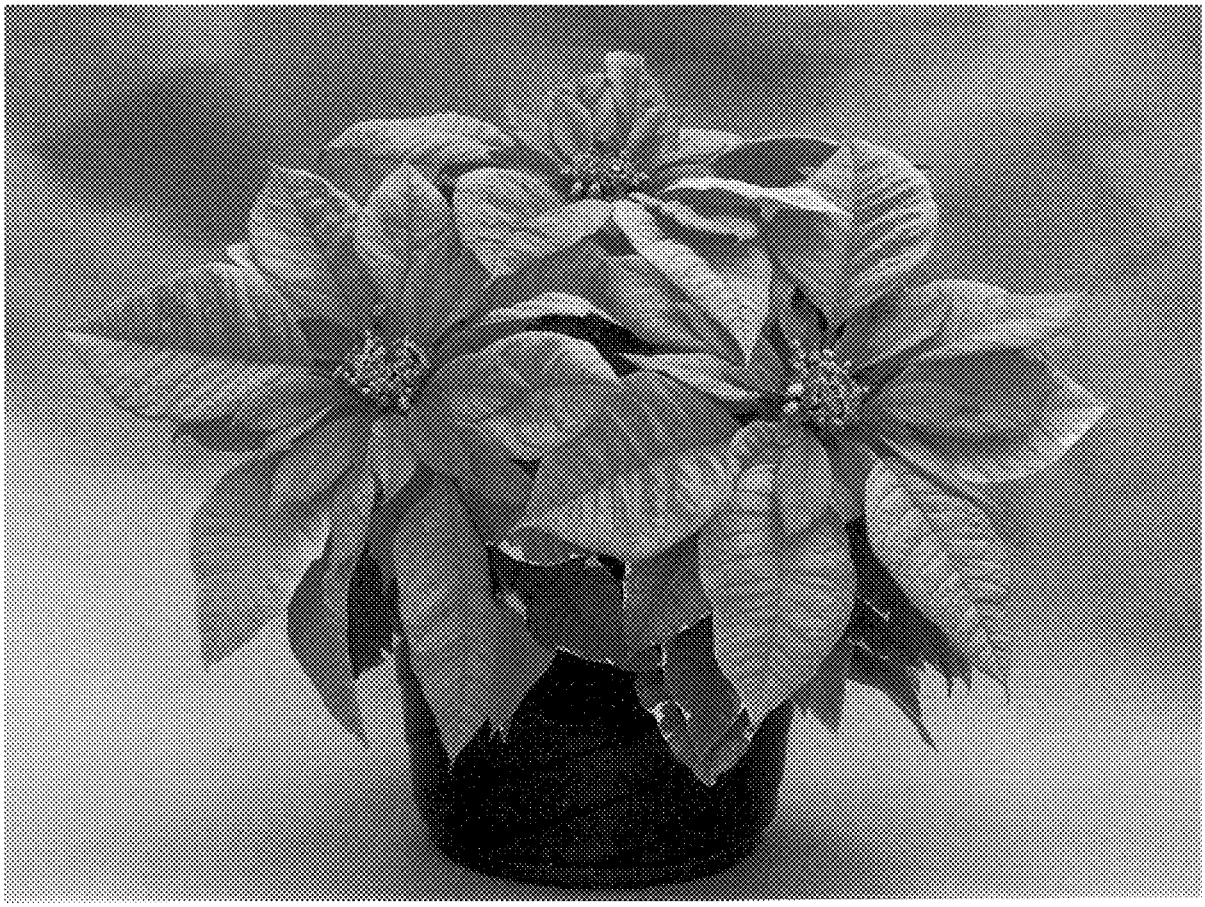

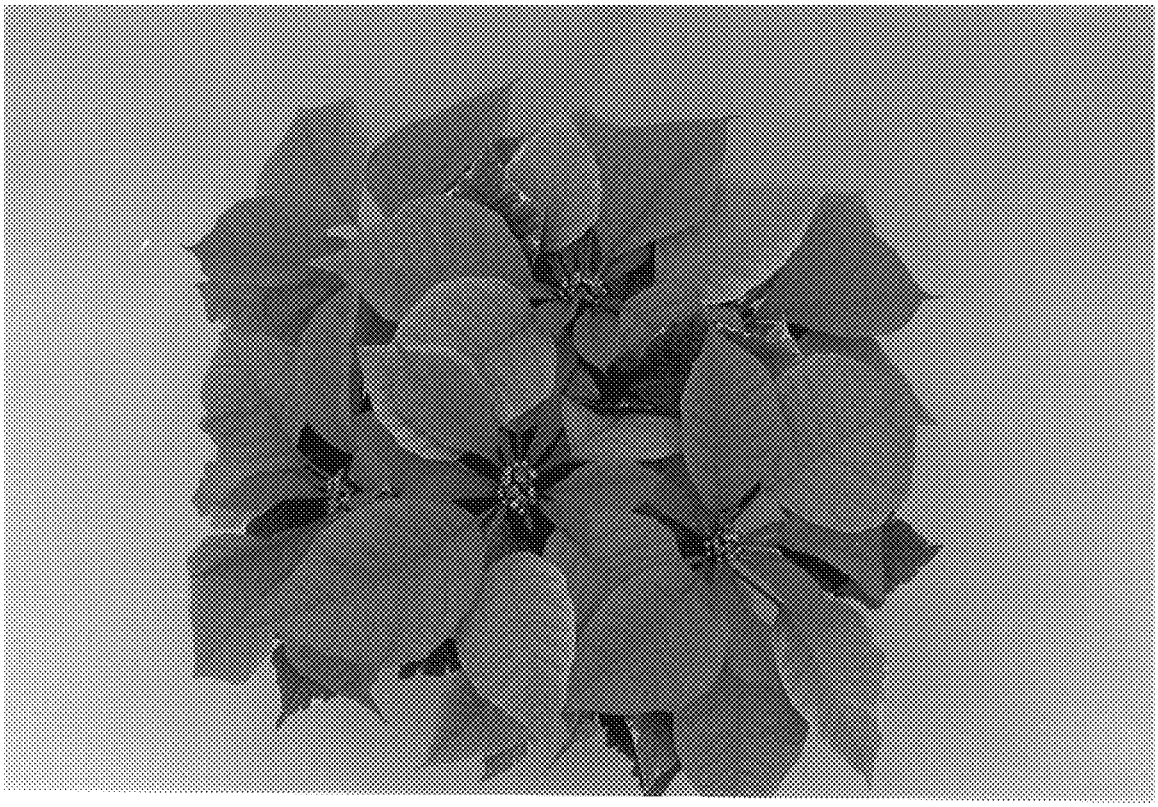
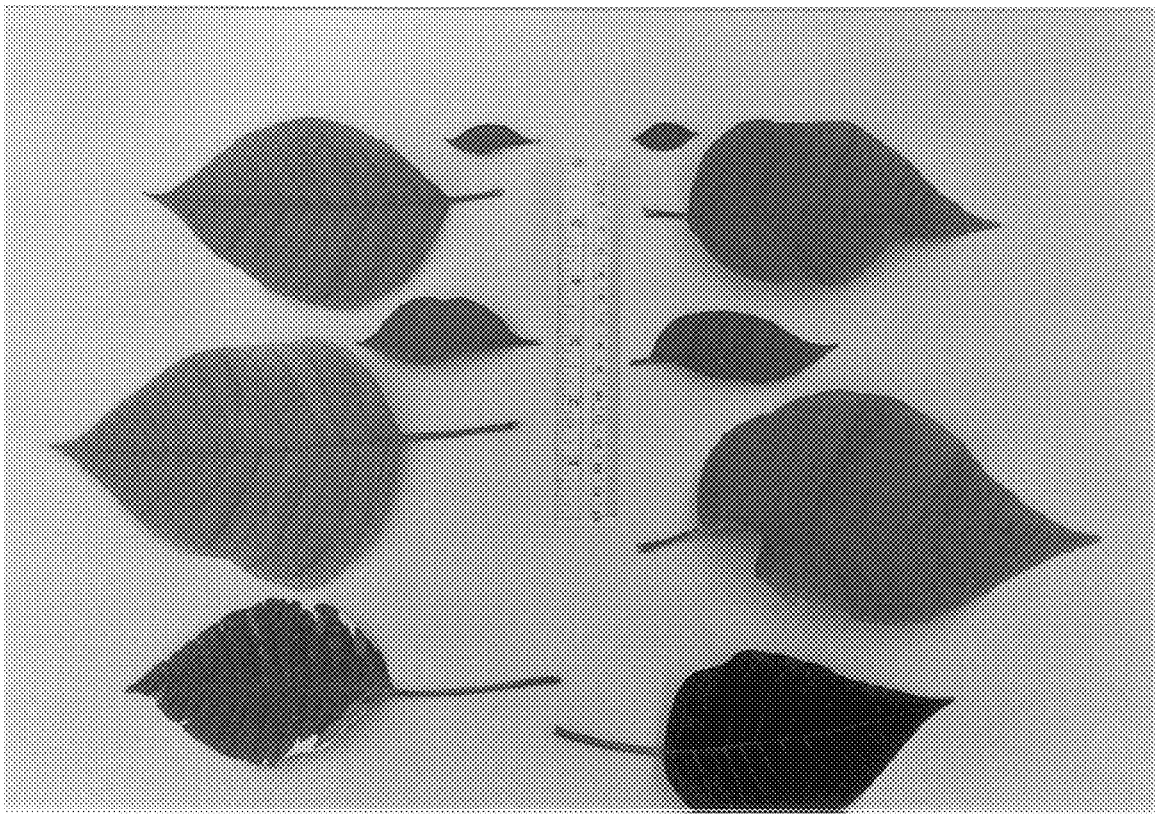

* * * * *